US008603989B2

United States Patent
Halperin

(10) Patent No.: US 8,603,989 B2
(45) Date of Patent: Dec. 10, 2013

(54) METHOD FOR TREATING AND PREVENTING KIDNEY STONES EMPLOYING AN SGLT2 INHIBITOR AND COMPOSITION CONTAINING SAME

(75) Inventor: Mitchell Halperin, Princeton, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 229 days.

(21) Appl. No.: 12/993,764

(22) PCT Filed: May 15, 2009

(86) PCT No.: PCT/US2009/044158
§ 371 (c)(1),
(2), (4) Date: Nov. 19, 2010

(87) PCT Pub. No.: WO2009/143021
PCT Pub. Date: Nov. 26, 2009

(65) Prior Publication Data
US 2011/0077213 A1    Mar. 31, 2011

Related U.S. Application Data

(60) Provisional application No. 61/055,453, filed on May 22, 2008.

(51) Int. Cl.
*A61K 31/7034* (2006.01)
*A61K 31/351* (2006.01)
*C07H 7/04* (2006.01)
*C07D 309/10* (2006.01)

(52) U.S. Cl.
CPC ............... *C07H 7/04* (2013.01); *C07D 309/10* (2013.01); *A61K 31/7034* (2013.01); *A61K 31/351* (2013.01)
USPC ............. 514/23; 514/460; 536/1.11; 549/417

(58) Field of Classification Search
None
See application file for complete search history.

(56) References Cited

U.S. PATENT DOCUMENTS

| 6,515,117 B2 * | 2/2003 | Ellsworth et al. ............ 536/17.2 |
| 2006/0063722 A1 * | 3/2006 | Washburn et al. .............. 514/23 |
| 2008/0004336 A1 * | 1/2008 | Gougoutas et al. ........... 514/460 |
| 2009/0131395 A1 * | 5/2009 | Antonelli et al. ........ 514/210.02 |
| 2011/0046087 A1 * | 2/2011 | Eickelmann et al. ........... 514/62 |

FOREIGN PATENT DOCUMENTS

| GB | 1 403 900 A | 8/1974 |
| WO | WO 2003/099836 A | 12/2003 |
| WO | WO 2006/062224 A | 6/2006 |
| WO | WO2007/093610 | * 8/2007 |

OTHER PUBLICATIONS

Alvarez et al., "Prevalence and Risk Factors for Urolithiasis in Primary Gout: Is a Reappraisal Needed?" The Journal of Rheumatology (2005) vol. 32 No. 11 pp. 2189-2191.*
Coe et al., "The Pathogenesis and Treatment of Kidney Stones" Medical Progress (1992) vol. 327 No. 16 pp. 1141-1152.*
"Dietary Reference Intakes for Energy, Carbohydrate, Fiber, Fat, Fatty Acids, Cholesterol, Protein, and Amino Acids" Food and Nutrition Board, Institute of Medicine of the National Academies, published 2005 by the National Academies Press, pp. 265-338.*
Borghi Loris et al.: "Urine volume: Stone risk factor and preventive measure," NEPHRON, vol. 81, No. Suppl. 1, Dec. 1999, p. 31-37.
Katsuno, K. et al.: "Sergliflozin, a novel selective inhibitor of low-affinity sodium glucose contransporter (SGLT2), validates the critical role of SGLT2 in renal glucose reabsorption and modulates plasma glucose level," The Journal of Pharmacology and Experimental Therapeutics, vol. 320, No. 1, pp. 323-330, Jan. 1, 2007.
Handlon, Anthony L.: "Sodium glucose co-transporter 2 (SGLT2) inhibitors as potential antidiabetic agents," Expert Opinion on Therapeutic Patents, vol. 15, No. 11, pp. 1531-1540, Jan. 1, 2005.

* cited by examiner

*Primary Examiner* — Eric S Olson
(74) *Attorney, Agent, or Firm* — McDonnell Boehnen Hulbert & Berghoff LLP

(57) ABSTRACT

Methods are provided for treating and/or preventing kidney stones, employing an SGLT2 inhibitor alone, or in combination with a supply of carbohydrate, and/or in combination with a diuretic agent. Additionally, compositions comprising an SGLT2 inhibitor, optionally with a supply of carbohydrate, and/or a combination of an SGLT2 inhibitor and a diuretic agent are provided in the instant invention and are provided for use in the inventive methods.

11 Claims, 3 Drawing Sheets

Indirect comparison of GSK 869,682 and Dapagliflozin PGS in healthy individuals

METHOD FOR TREATING AND PREVENTING KIDNEY STONES EMPLOYING AN SGLT2 INHIBITOR AND COMPOSITION CONTAINING SAME

FIELD OF THE INVENTION

The invention relates to methods for treating and preventing kidney stones, comprising administering an SGLT2 inhibitor alone or in combination with a carbohydrate and/or a diuretic agent, and to compositions thereof.

BACKGROUND OF THE INVENTION

Kidney stone is a common human malady. Kidney stones, also called renal calculi, are solid crystal aggregations of dissolved minerals in urine. Most common kidney stones are caused by the precipitation of calcium compounds, particularly calcium oxalate, from super-saturated solutions normally stabilized against precipitation by glycoproteins. However, certain factors cause the stabilizing function to break down whereby precipitation occurs with resulting deposition of solid calcium compounds, which accumulate to cause blockages in the kidney, bladder or elsewhere in the urinary tract. Kidney stones typically leave the body by passage in the urine. If stones grow to sufficient size before passage, they can cause blockages of the ureter. Such blockages may cause extreme pain and discomfort most commonly felt in the flank, lower abdomen and groin.

In addition to excruciating pain, symptoms of kidney stones may also include blood in the urine due to minor damage to inside lining of kidney, ureter and urethra; reduced urine volume caused by obstruction of the bladder or urethra by the stones; kidney infection as a result of stone blockage; abdominal distention; nausea or vomiting; and fever and chills. Most kidney stones 4 mm or less in size do not require surgery and will pass on their own; however, the vast majority of stones greater than 6 mm will require some form of intervention. Common measures to facilitate the passage of a stone include increased hydration, medication for treating infection and reducing pain, and diuretics to encourage urine flow and prevent further stone formation. Immediate surgery may be required in situations where patients have only one working kidney, or patients experience intractable pain, kidney infection, or are at risk of rapidly developing severe sepsis and toxic shock. In most cases where surgery is needed, non-invasive Extracorporeal Shock Wave Lithotripsy (ESWL) will be used, which may lead to bleeding and pain related to passage of stone fragment. If non-invasive measures fail, a more invasive procedure such as ureteroscopic fragmentation using laser, ultrasonic or mechanical forms of energy to fragment the larger stones may be required.

Patients that are at risk of forming kidney stones or are frequent stone formers are instructed to modify diet or increase water consumption. Increased water consumption dilutes the concentration of lithogenic substances in the kidney and reduces the likelihood of crystal formation. Intermittent water consumption, however, only leads to intermittent increase in urine volume. This is particularly problematic at night when patients are neither eating nor drinking, and urine tends to become more concentrated than during the day, thereby favoring crystal formation. Thus, there remains a need for a simple and effective method and composition for preventing and treating kidney stone.

SUMMARY OF THE INVENTION

This invention provides methods and reagents for preventing and treating kidney stones by inhibiting a sodium glucose transporter expressed in the kidney called SGLT2. SGLT2 is a member of a family of proteins that utilizes an electrochemical sodium gradient to transport glucose, against the sodium concentration gradient inside the cells. Different Na+/Glucose transporters are found in different tissues: SGLT1 is mainly found in intestinal mucosa in the small intestine and the S3 segment of the proximal tubule of the nephron in the kidney; and SGLT2 is mainly found in the S1 segment of the proximal tubule of the nephron in the kidney. As set forth herein, SGLT2 inhibitors increase urine excretion of glucose. This increase in osmotic excretion is beneficial as a treatment or prevention for kidney stones.

In one aspect, the invention provides methods for treating and/or preventing kidney stones in a mammal comprising administering to the mammal in need of such treatment a therapeutically effective amount of an SGLT2 inhibitor. In one embodiment, the SGLT2 inhibitor is dapagliflozin (compound I). In yet another embodiment, the SGLT2 inhibitor compound is dapagliflozin PGS (compound Ia). In certain embodiments of this aspect, the methods of the invention for treating and/or preventing kidney stones in a mammal comprise administering to the mammal in need thereof a pharmaceutical composition comprising a therapeutically effective amount of SGLT2 inhibitor, and optionally at least one pharmaceutically-acceptable carrier, excipient or diluent.

In another aspect, the invention provides methods for treating and/or preventing kidney stones in a mammal comprising administering to the mammal in need of such treatment a therapeutically effective amount of an SGLT2 inhibitor and a supply of carbohydrate. The carbohydrate can be supplied prior to, after, or concurrently with the SGLT2 inhibitor and the diuretic agent. In a further aspect, these methods of the invention comprise administering to the mammal, in addition to a therapeutically effective amount of an SGLT2 inhibitor, a diuretic agent where the diuretic agent is administered prior to, after, or concurrently with the SGLT2 inhibitor. In a particular embodiment of the invention, the diuretic agent is an ADH antagonist. In yet another embodiment, the methods of the invention comprises administering to the mammal a therapeutically effective amount of an SGLT2 inhibitor, a supply of carbohydrate, and a diuretic agent. In certain embodiments of this aspect, the methods of the invention for treating and/or preventing kidney stones in a mammal comprise administering to the mammal in need thereof a pharmaceutical composition comprising a therapeutically effective amount of SGLT2 inhibitor, a supply of carbohydrate or a diuretic agent or both a supply of carbohydrate and a diuretic agent, and at least one pharmaceutically-acceptable carrier, excipient or diluent.

In a further aspect, the invention provides pharmaceutical compositions for treating and/or preventing kidney stones comprising an SGLT2 inhibitor and a diuretic agent. In one embodiment, the pharmaceutical compositions further comprise at least one pharmaceutically-acceptable carrier, excipient or diluent.

In another aspect, the invention provides pharmaceutical compositions for treating and/or preventing kidney stones comprising an SGLT2 inhibitor and a source of carbohydrate or a diuretic agent or both a source of carbohydrate and a diuretic agent. In one embodiment, the pharmaceutical compositions further comprise at least one pharmaceutically-acceptable carrier, excipient or diluent.

Specific preferred embodiments of the present invention will become evident from the following more detailed description of certain preferred embodiments and the claims.

BRIEF DESCRIPTION OF THE FIGURES

The invention is illustrated by reference to the accompanying drawings described below.

DETAILED DESCRIPTION OF THE INVENTION

Figure 1:
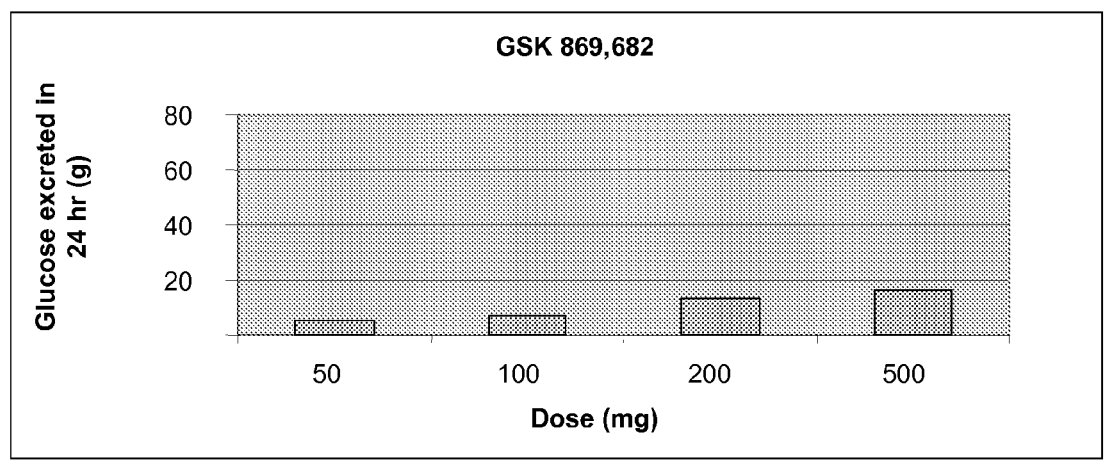
FIG. 1 shows two bar graphs comparing urine glucose excretion in healthy individuals that were treated with GSK 869,682 (top panel) and dapagliflozin PGS (bottom panel).
Figure 1:
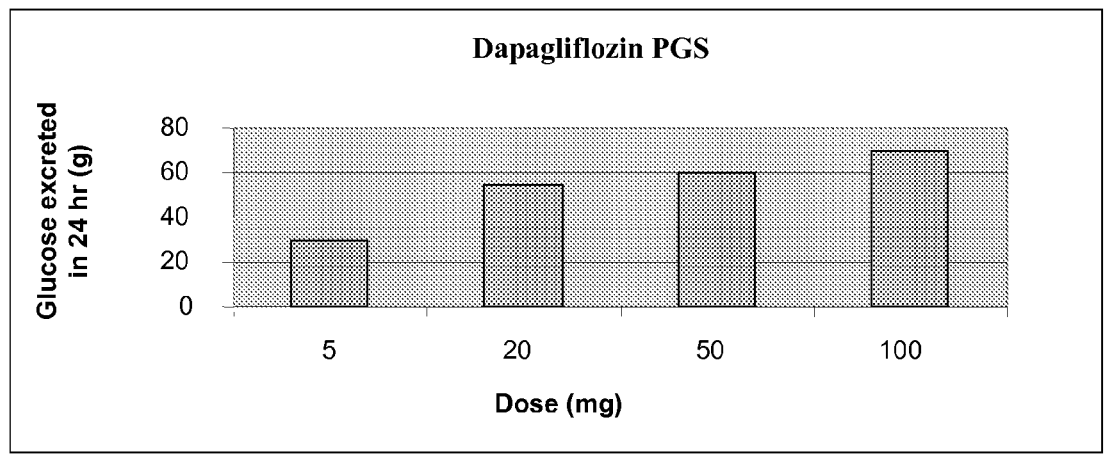

The invention thus provides methods and reagents directed towards treating and/or preventing kidney stones in a mammal in need thereof. In particular, these methods and reagents are capable of facilitating the passing of kidney stones and reducing the propensity of kidney stone formation in the mammal.

In one aspect, the invention provides methods for treating and/or preventing kidney stones in a mammal comprising administering to the mammal in need of such treatment a therapeutically effective amount of a sodium glucose transporter 2 (SGLT2) inhibitor. In another aspect, the invention provides methods for treating and/or preventing kidney stones in a mammal further comprising administering to the mammal at least one additional reagent that facilitates and enhances the effects of the SGLT2 inhibitor on the prevention and treatment of kidney stones. In certain embodiments, the methods of the invention for treating and/or preventing kidney stones further comprise administering to the mammal in need thereof a supply of carbohydrate. In certain embodiments of this aspect, the methods of the invention for treating and/or preventing kidney stones in a mammal comprise administering to the mammal in need thereof a pharmaceutical composition comprising a therapeutically effective amount of SGLT2 inhibitor, optionally a supply of carbohydrate, and further optionally at least one pharmaceutically-acceptable carrier, excipient or diluent.

In certain embodiments, the mammal is a human. In alternative embodiments, the mammal is a non-human mammal. In yet other embodiments, the mammal has recurrent kidney stones, or has high propensity for kidney stone formation, and the present invention provides methods for preventing kidney stone formation.

In another aspect, the invention provides methods for treating and/or preventing kidney stones in a mammal comprising administering to the mammal in need of such treatment a therapeutically effective amount of a sodium glucose transporter 2 (SGLT2) inhibitor and a diuretic agent wherein the diuretic agent is administered before, after, or concurrently with the SGLT2 inhibitor. In certain embodiments, the invention provides methods for treating and/or preventing kidney stones in a mammal comprising administering to the mammal in need of such treatment a therapeutically effective amount of a SGLT2 inhibitor, a supply or carbohydrate, and a diuretic agent.

In certain embodiments of this aspect, the methods of the invention for treating and/or preventing kidney stones in a mammal comprise administering to the mammal in need thereof a pharmaceutical composition comprising a therapeutically effective amount of SGLT2 inhibitor and a supply of carbohydrate or a diuretic agent or both a carbohydrate and a diuretic agent, and optionally at least one pharmaceutically-acceptable carrier, excipient or diluent. In one embodiment, the diuretic agent is an ADH antagonist. The terms "ADH antagonist" and "vasopressin antagonist" are used interchangeably throughout the application.

In yet another aspect, the invention provides a SGLT2 inhibitor for use in therapy in treating and/or preventing kidney stones. In a further aspect, the invention provides the use of a SGLT2 inhibitor in the manufacture of a medicament for treatment and/or prevention of kidney stones. In a further aspect, the invention provides a combination of a SGLT2 inhibitor and a supply of carbohydrate or a diuretic agent or a supply of carbohydrate and a diuretic agent as a medicament for the treatment and/or prevention of kidney stones. In another aspect, the invention provides use of a SGLT2 inhibitor in the manufacture of a medicament for treatment and/or prevention of kidney stones, in which such treatment or prevention comprises a combination with a supply of carbohydrate or a diuretic agent or a supply of carbohydrate and a diuretic agent, for concurrent or sequential use. In certain embodiments, the supply of carbohydrate and/or the diuretic agent is used sequentially, either before or after the treatment with the SGLT2 inhibitor. In certain embodiments, the diuretic agent is an ADH antagonist.

ADH antagonists suitable for use in the current invention include, but are not limited to, aquaretics class of compounds. Examples of aquaretic ADH antagonist include, without limitation, OPC-31260, conivaptan (VAPRISOL), tolyaptan, tolvaptan, lixivaptan, lixiyaptan, and SR-121463.

The term "aquaretics" as used herein refers to a class of compounds that promote water excretion without electrolyte loss. Aquaretics include natural as well as synthetic aquaretics. Synthetic aquaretics are usually ADH antagonists.

The term "a supply of carbohydrate," or "a source of carbohydrate" as used herein refers to simple or complex carbohydrate either from the daily intake of carbohydrate in the diet or from a supplement formulated with the SGLT2 inhibitor of the present invention or provided in conjunction with the SGLT2 inhibitor. A source of carbohydrate can be used advantageously with the SGLT2 inhibitor of the present invention to increase urine volume. Non-limiting examples of carbohydrate include monosaccharide such as glucose, disaccharides such as sucrose, and complex oligosaccharides or polysaccharides such as starch. The supply of carbohydrate can be provided to the mammal in need of the kidney stone treatment or prevention before, after, or concurrent with the SGLT2 inhibitor. The carbohydrate of the current invention can be supplied in the range of about 30 to about 270 g per day, preferably in the range of about 60 to about 180 g per day, and most preferably about 90 g, or close to about one third of the mammal's daily carbohydrate intake per day. It is within the knowledge of one skilled artisan or physician to determine the suitable amount of carbohydrate to be used in the present invention.

The methods of this invention can be used to treat and/or prevent kidney stones in non-diabetic as well as diabetic patients. In one embodiment, the SGLT2 inhibitors employed in the above-defined methods of the invention will not cause hypoglycemia in a non-diabetic mammal, i.e. a mammal that does not suffer from hyperglycemia. In another embodiment, the SGLT2 inhibitors employed in the above-defined methods of the invention will not cause hypoglycemia in a diabetic mammal. It will be understood by the skilled worker that administered amounts and in vivo concentrations of the SGLT2 inhibitors used according to the methods of the invention can be chosen to have anti-kidney stones effects without disturbing the recipient's plasma glucose homeostasis.

Thus, in carrying out the methods of the invention for treating and/or preventing kidney stones, the SGLT2 inhibitor can be administered to a patient in need of such treatment in a dose which can be as high as that used to treat and/or prevent kidney stones but less than an amount which could cause hypoglycemia. The daily dose can be lowered as successful treatment or prevention of kidney stones is achieved. For example, depending upon the patient, and the specific SGLT2 inhibitor employed, the SGLT2 inhibitor can be orally administered in a kidney stones treating or preventing amount from about 1 to about 1000 mg per day, preferably from about 2 to about 400 mg/day, preferably 2.5 to about 75 mg/day, and more preferably 20 to about 50 mg/day, which can be administered in a single dose or in the form of individual doses from 1 to 4 times per day.

In certain embodiments of the methods of the invention, the SGLT2 inhibitor is advantageously administered in conjunction with a supply of carbohydrate to a mammal in need of a kidney stones treatment. Without being limited to particular mechanisms, the combination of an SGLT2 inhibitor and a supply of carbohydrate can further promote osmotic excretion of glucose and thus increase water release in the urine, as well as minimize the risk of the development of hypoglycemia.

The invention also provides pharmaceutical compositions or pharmaceutical combinations for treating and/or preventing kidney stones comprising a therapeutically effective amount of an SGLT2 inhibitor. In yet another aspect, the invention provides pharmaceutical compositions for treating and/or preventing kidney stones comprising a therapeutically effective amount of an SGLT2 inhibitor and a diuretic agent. Advantageously, the pharmaceutical composition may further comprise a supply of carbohydrate. In certain embodiments of this aspect, the SGLT2 inhibitor is dapagliflozin. In further embodiments, the SGLT2 inhibitor is dapagliflozin PGS. In certain other embodiments, the SGLT2 inhibitor is remogliflozin, remogliflozin etabonate, sergliflozin or sergliflozin etabonate.

Other SGLT2 inhibitors suitable for use in this aspect of the invention are described throughout the specification, including without limitation AVE2268, TS-033, YM-543, BI 10773, BI 44847, and TA-7284. In certain embodiments, the pharmaceutical compositions further comprise at least one pharmaceutically-acceptable carrier, excipient or diluent. The invention provides methods for treating and/or preventing kidney stones comprising administering to a mammal in need thereof a pharmaceutical composition of the invention.

The SGLT2 inhibitors suitable for use in accordance with the invention also can be administered by injection to a patient in a kidney stones treating or preventing amount from about 1 to about 100 mg/day, preferably from about 1 to about 30 mg/day.

The SGLT2 inhibitors employed in the invention are most preferably selective for SGLT2 relative to SGLT1. High selectivity for SGLT2, as is the case with dapagliflozin, is advantageous for use in the current invention because it avoids the unpredictable effects of intestinal SGLT1 inhibition.

Selectivity for SGLT2 of a given inhibitor can be determined by comparing the $EC_{50}$ values measured in the SGLT1 and SGLT2 assay. Briefly, Human SGLT1 (hSGLT1) and human SGLT2 (hSGLT2) full-length cDNA sequences were cloned by PCR using MARATHON READY™ human kidney cDNA (Clontech, Mountain View, Calif.), with primers designed from published sequences (Genbank accession numbers NM_003041 and NM_000343). The hSGLT1 and hSGLT2 sequences were cloned into pIRESneo vector (Clontech, Mountain View, Calif.) for mammalian expression and were stably transfected into Chinese hamster ovary (CHO) cells. SGLT-expressing clones were selected based on resistance to G418 antibiotic (GENETICIN®, Invitrogen, Carlsbad, Calif.) and activity in the $^{14}$C-α-methyl-D-glucopyranoside ($^{14}$C-AMG) uptake assay.

Cells expressing hSGLT1 or hSGLT2 were maintained using standard cell culture techniques. Assays for sodium-dependent glucose transport in 96-well plates were initiated by adding 100 μl/well of protein-free assay buffer containing sodium (Hepes/Tris pH 7.4, 137 mM NaCl, 5.4 mM KCl, 2.8 mM $CaCl_2$, 1.2 mM $MgSO_4$), 10 μM $^{14}$C-AMG and inhibitor or dimethyl sulfoxide (DMSO) vehicle, and plates were incubated for 2 h at 37° C. Sodium-dependent $^{14}$C-AMG uptake was calculated by subtracting the counts per minute (CPM) observed under sodium-free uptake conditions from the counts observed under sodium-containing conditions. Inhibitors were assayed at various concentrations in triplicate in the presence of sodium, and the percent inhibition was calculated by comparing CPM in inhibitor-containing wells with CPM in wells containing only DMSO vehicle. Phlorizin, a known SGLT inhibitor, was evaluated in parallel in every assay. A dose-response curve was fitted to an empirical four-parameter model using XL Fit (IDBS, Guilford, UK) to determine the inhibitor concentration at half-maximal response ($EC_{50}$). SGLT2 selectivity is represented as a ratio of $EC_{50}$ in favor of SGLT2. An SGLT2 inhibitor with an $EC_{50}$ selective ratio of at least 10, and more preferably at least 100, in favor of SGLT2 is suitable for use in the instant invention.

The SGLT2 inhibitors suitable for use in accordance with the invention comprise C-arylglucosides or O-arylglucosides. SGLT2 inhibitors C-arylglucosides and O-arylglucosides are effective in treating diabetes. See U.S. Pat. No. 6,774,112, which is incorporated herein by reference in its entirety. As disclosed herein, it was unexpectedly discovered that this class of SGLT2 inhibitors not only can increase glucose excretion in urine, but can also increase urine volume. Urinary excretion of glucose requires concomitant excretion of electrolyte-free water so that the final outcome produces a diuresis without releasing sodium to the urine. Without being limited to a particular mechanism, the methods of the invention using an SGLT2 inhibitor provide an effective treatment for kidney stone partly because it promotes a gradual release of electrolyte-free water in the process of glucose excretion in the urine. To the Applicant's knowledge, no other known anti-diabetic drugs in humans can cause glucoseuria. Advantageously and unexpectedly, this class of SGLT2 inhibitors of the current invention increases urine volume over time. The increased urine volume facilitates the passing of kidney stones through urine, and dilutes the concentrations of stone-forming substances in the kidney, nephrons, ureter, and renal pelvis, and thus reduces the propensity of kidney stone formation. In certain embodiment of the invention, the SGLT2 inhibitor is a C-aryl glucoside.

Examples of C-arylglucoside (also referred to as C-glucosides) SGLT2 inhibitors which can be employed in the method of the invention, include, but are not limited to the following:

1) C-aryl glucosides as disclosed in U.S. Pat. Nos. 6,515,117 and 6,414,126, the disclosures of which are incorporated herein by reference in their entirety for any purpose;

2) C-aryl glucosides as described in U.S. patent application Ser. No. 11/233,617 (U.S. Patent Application Publication No. 2006/0063722 A1), the disclosure of which is incorporated herein by reference in its entirety;

3) C-aryl glucosides described in U.S. Pat. No. 6,774,112, the disclosure of which is incorporated herein by reference in its entirety;

4) Glucopyranosyl-substituted benzene derivatives as disclosed in U.S. Patent Application Publication No. 2005/0209166, the disclosure of which is incorporated herein by reference in its entirety;

5) D-pyranosyl-substituted phenyl compounds as disclosed in U.S. Patent Application Publication No. 2006/0074031, the disclosure of which is incorporated herein by reference in its entirety;

6) D-xylopyranosyl-substituted compounds as disclosed in U.S. Patent Application Publication No. 2006/0035841, the disclosure of which is incorporated herein by reference in its entirety;

7) D-xylopyranosyl-substituted phenyl compounds as disclosed in U.S. Patent Application Publication No. 2006/0009400, the disclosure of which is incorporated herein by reference in its entirety;

8) D-glucopyranosyl-phenyl-substituted compounds as disclosed in U.S. Patent Application Publication No. 2006/0025349, the disclosure of which is incorporated herein by reference in its entirety;

9) C-glycoside derivatives as disclosed in U.S. Patent Application Publication No. 2006/0122126, the disclosure of which is incorporated herein by reference in its entirety; and 10) D-xylopyranosyl-substituted phenyl compounds as disclosed in U.S. Patent Application Publication No. 2006/0019948, the disclosure of which is incorporated herein by reference in its entirety.

Examples of O-glucoside SGLT2 inhibitors which can be employed in the methods and pharmaceutical compositions of the invention include, but are not limited to those described in the following:

1) 5-Thio-β-D-glucopyranoside as disclosed in U.S. Patent Application Publication No. 2006/0194809, the disclosure of which is incorporated by reference in its entirety for any purpose;

2) Glucopyranyloxybenzene derivatives of as disclosed in WO 03/01180, the disclosure of which is incorporated by reference in its entirety for any purpose;

3) Pyrazole derivatives as disclosed in U.S. Pat. No. 6,908,905, the disclosure of which is incorporated herein by reference for any purpose;

4) Pyrazole compounds as disclosed in U.S. Pat. No. 6,815,428, the disclosure of which is incorporated herein by reference for any purpose;

5) O-glucosylated benzamide compounds as disclosed in U.S. Pat. No. 6,555,519, the disclosure of which is incorporated herein by reference in its entirety for any purpose; and 6) O-arylglucoside (or O-glucoside) compounds as disclosed in U.S. Pat. No. 6,683,056, the disclosure of which is incorporated herein by reference in its entirety for any purpose.

Other O-aryl glucosides SGLT2 inhibitors which can be used in the invention are disclosed in the following references, each of which is incorporated herein by reference in its entirety for any purpose. EP 598359A1, EP 0850948A1, JP 09188625A, JP 09124685A, JP 09124684, EP 773226-A1, and JP 08027006-A, EP 684254-A1.

Other disclosures and publications disclosing SGLT2 inhibitors that can be employed in the methods and pharmaceutical compositions of the invention are as follows: K. Tsujihara et al., *Chem. Pharm. Bull.*, 44:1174-1180 (1996); M. Hongu et al., *Chem. Pharm. Bull.*, 46:22-33 (1998); M. Hongu et al., *Chem. Pharm. Bull.*, 46:1545-1555 (1998); and A. Oku et al., *Diabetes*, 48:1794-1800 (1999) and JP 10245391 (Dainippon).

Preferred SGLT2 inhibitors that can be employed in the present invention include dapagliflozin, remigliflozin, antisense oligonucleotide ISIS 388626, sergliflozin and those disclosed in U.S. Patent Application Publication No. 2005/0233982 (Boehringer Ingelheim Corp.), U.S. Patent Application Publication No. 2005/0119192 (Kissei Pharmaceutical Co.), WO 2006/035796 (Kissei Pharmaceutical Co.), JP 2006/117651 (Taisho Pharmaceutical Co.), JP 2004/4359630 (Yamanouchi Pharmaceutical Co.), WO 2006/080421 (Chugai Seiyaku Kabushiki Kaishi), U.S. Patent Application Publication No. 2005/0233988 (Tanabe Seiyaku Co.), WO 2005/012321 (Tanabe Seiyaku Co.), U.S. Pat. No. 7,015,201 (Ajinomoto Co.), WO 2006/058597 (Merck Patent GmbH), WO 2006/011469 (Chugai Seiyaku Kabushiki Kaisha), U.S. Patent Application Publication No. 2003/0195235 (Johnson & Johnson), and WO 2006/037537 (Boehringer Ingelheim), the disclosure of each of which is herein incorporated by reference in its entirety for any purpose.

In a preferred aspect, the invention provides SGLT2 inhibitors for use in the methods and pharmaceutical compositions of the invention that are disclosed in U.S. Pat. Nos. 6,414,126 and 6,515,117, more preferably the SGLT2 inhibitor is compound I or dapagliflozin

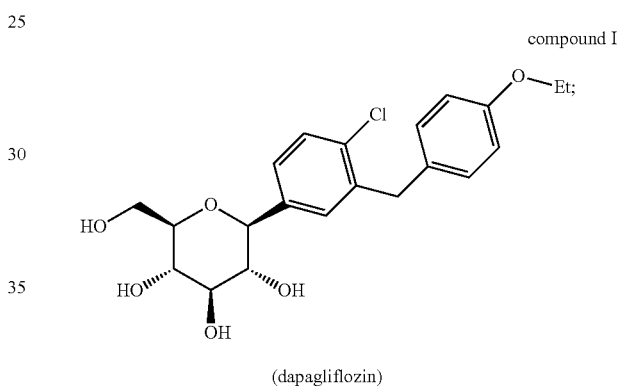

(dapagliflozin)

or a pharmaceutically acceptable salt thereof, all stereoisomers thereof, or a prodrug ester thereof.

In another preferred aspect, the invention provides an SGLT2 inhibitor for use in the methods and pharmaceutical compositions of the invention that is compound IIIA compound IIIA or a pharmaceutically acceptable salt thereof, all stereoisomers thereof, or a prodrug ester thereof.

In another preferred aspect, the invention provides an SGLT2 inhibitor for use in the methods and pharmaceutical compositions of the invention that is compound II

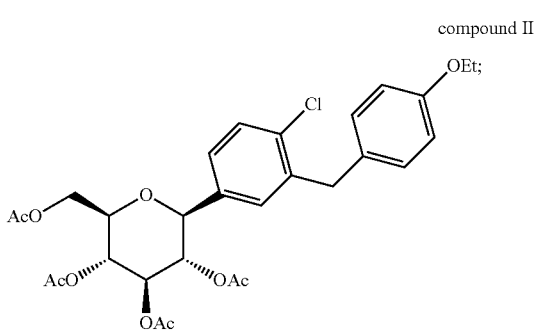 [SMILES: CCOc1ccc(Cc2cc([C@@H]3O[C@H](COC(C)=O)[C@@H](OC(C)=O)[C@H](OC(C)=O)[C@H]3OC(C)=O)ccc2Cl)cc1]

compound II or a pharmaceutically acceptable salt thereof, all stereoisomers thereof, or a prodrug ester thereof.

In another preferred aspect, the invention provides crystalline forms of compound I including the crystalline forms disclosed in U.S. application Ser. No. 11/765,481, the disclosure of which is incorporated herein by reference in its entirety for any purpose. A most preferred crystalline form for use in the methods and pharmaceutical compositions of the invention is the (S)-propylene glycol solvate of the compound of formula I, namely Compound Ia or dapagliflozin PGS

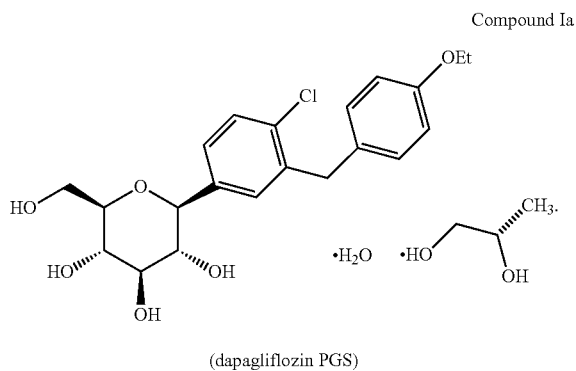

Compound Ia (dapagliflozin PGS)

Compound Ia or dapagliflozin PGS is prepared as described in U.S. application Ser. No. 11/765,481, published as U.S. Patent Application Publication No. 2008/0004336, which is incorporated by reference herein. Prior to the instant application, it was not appreciated that any of the above disclosed SGLT2 inhibitors could be used for effective treatment of kidney stones.

The SGLT2 inhibitor employed in accordance with the invention can be administered to various mammalian species, such as dogs, cats, cattle, humans, etc., in need of treatment. These agents can be administered systemically, such as orally or parenterally.

The invention also provides pharmaceutical compositions that comprise compounds of the invention formulated together with one or more non-toxic pharmaceutically acceptable carriers. The pharmaceutical compositions can be specially formulated for oral administration in solid or liquid form, for parenteral injection or for rectal administration.

The pharmaceutical compositions of this invention can be administered to humans and other mammals orally, rectally, parenterally, intracisternally, intravaginally, intraperitoneally, bucally or as an oral or nasal spray. The term "parenterally," as used herein, refers to modes of administration which include intravenous, intramuscular, intraperitoneal, intrasternal, subcutaneous and intraarticular injection and infusion.

The SGLT2 inhibitor can be incorporated in a conventional systemic dosage form, such as a tablet, capsule, elixir or injectable formulation. The above dosage forms will also include the necessary physiologically acceptable carrier material, excipient, lubricant, buffer, antibacterial, bulking agent (such as mannitol), antioxidants (ascorbic acid or sodium bisulfite) or the like. Oral dosage forms are preferred, although parenteral forms are quite satisfactory as well.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), vegetable oils (such as olive oil), injectable organic esters (such as ethyl oleate) and suitable mixtures thereof. Proper fluidity can be maintained, for example, by the use of coating materials such as lecithin, by the maintenance of the required particle size in the case of dispersions and by the use of surfactants.

These compositions may also contain adjuvants such as preservative, wetting agents, emulsifying agents and dispersing agents. Prevention of the action of microorganisms can be ensured by the inclusion of various antibacterial and antifungal agents, for example, paraben, chlorobutanol, phenol sorbic acid and the like. It may also be desirable to include isotonic agents such as sugars, sodium chloride and the like. Prolonged absorption of the injectable pharmaceutical form can be brought about by the inclusion of agents which delay absorption such as aluminum monostearate and gelatin.

In some cases, in order to prolong the effect of the drug, it is desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In such solid dosage forms, the active compound is mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e)

solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions may also include adjuvants such as wetting agents, emulsifying and suspending agents, sweetening, flavoring and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, tragacanth and mixtures thereof.

The dose administered is adjusted according to the age, weight, and condition of the patient, as well as the route of administration, dosage form and regimen, and the desired result. In general, the dosage forms described above can be administered containing amounts of SGLT2 inhibitor of from about 1 to about 1000 mg per day preferably from about 2 to about 400 mg per day, in single or divided doses of one to four times daily.

Diuretics or diuretic agents as used herein refer to agents or compounds that promote excretion of urine. Diuretic agents which can be employed in conjunction with the SGLT2 inhibitors, in accordance with the invention, can be administered in the same or different dosage forms with the SGLT2 inhibitor.

Suitable diuretic agent for use in the claimed invention includes, but is not limited to direct diuretic, indirect diuretic, loop diuretic, osmotic diuretic, and potassium sparing diuretic. Specific examples of diuretics suitable for use in the current invention include, but are not limited to, ADH antagonist, ammonium chloride, glycerin, isosorbide, dichlorphenamide, methazolamide, acetazolamide, acetazolamide sodium, benzothiadiazine, bendroflumethiazide, benzthiazide, chlorthalidone, chlorothiazide, cyclothiazide, hydrochlorothiazide, hydroflumethiazide, indapamide, methylclothiazide, metolazone, polythiazide, quinethazone, tricholomethiazide, amiloride hydrochloride, spironolactone, triamterene, bumetamide, ethacrynic acid, ethacrynate sodium, furosemide, and torsemide (Remington: the Science and Practice of Pharmacy, $21^{st}$ ed. 2005, Lippincott Williams & Wilkins, Philadelphia, Pa.). Diuretic agents approved by the FDA such as those listed in the Physicians' Desk Reference ($61^{st}$ Ed. (2007)) can also be employed for use in the instant invention. Diuretics most suitable for use in the current invention include loop diuretics, such as furosemide, bumetianide, torsemide, and ethacynic acid.

SGLT2 inhibitors are employed in a weight ratio to the optional diuretic agent in an amount within the range from about 200:1 to about 0.1:1, preferably from about 100:1 to about 0.2:1.

Dosages for the diuretic agent (used in combination with the SGLT2 inhibitor) are preferably the recommended doses for such diuretic agents as disclosed in the latest PHYSICIANS' DESK REFERENCE (PDR) or REMINGTON'S PHARMACEUTICAL SCIENCES (Mack Publishing Co., Easton, Pa.).

Unless otherwise indicated, dosages and formulations for SGLT2 inhibitors used in the methods set forth herein are disclosed in the various patents and applications discussed throughout the application, which are incorporated herein by reference in their entireties.

The various formulations of the invention can optionally include one or more fillers or excipients in an amount within the range of from about 0 to about 90% by weight and preferably from about 1 to about 80% by weight such as lactose, sugar, corn starch, modified corn starch, mannitol, sorbitol, inorganic salts such as calcium carbonate and/or cellulose derivatives such as wood cellulose and microcrystalline cellulose.

One or more binders can be present in addition to or in lieu of the fillers in an amount within the range of from about 0 to about 35% and preferably from about 0.5 to about 30% by weight of the composition. Examples of such binders suitable for use herein include polyvinylpyrrolidone (molecular weight ranging from about 5000 to about 80,000 and preferably about 40,000), lactose, starches such as corn starch, modified corn starch, sugars, gum acacia and the like as well as a wax binder in finely powdered form (less than 500 microns) such as carnauba wax, paraffin, spermaceti, polyethylenes or microcrystalline wax.

Where the composition is in the form of a tablet, it may include one or more tabletting lubricants in an amount within the range of from about 0.2 to about 8% and preferably from about 0.5 to about 2% by weight of the composition, such as magnesium stearate, stearic acid, palmitic acid, calcium stearate, talc, carnauba wax and the like. Other conventional ingredients that can optionally be present include preservatives, stabilizers, anti-adherents or silica flow conditioners or glidants, such as Syloid brand silicon dioxide as well as FD&C colors.

Tablets of the invention can also include a coating layer that can comprise from 0 to about 15% by weight of the tablet composition. The coating layer can comprise any conventional coating formulations and include one or more film-formers or binders, such as a hydrophilic polymer like hydroxypropylmethylcellulose, and/or a hydrophobic polymer like methacrylic acid esters neutral polymer, ethyl cellulose, cellulose acetate, polyvinyl alcohol-maleic anhydride copolymers, β-pinene polymers, glyceryl esters of wood resins and the like and one or more plasticizers, such as triethyl citrate, diethyl phthalate, propylene glycol, glycerin, butyl phthalate, castor oil and the like. Both core tablets as well as coating formulations can contain aluminum lakes to provide color.

The film formers are applied from a solvent system containing one or more solvents including water, alcohols like methyl alcohol, ethyl alcohol or isopropyl alcohol, ketones like acetone, or ethylmethyl ketone, chlorinated hydrocarbons like methylene chloride, dichloroethane, and 1,1,1-trichloroethane.

Where a color is employed, the color is applied together with the film former, plasticizer and solvent compositions.

It will be recognized by one of skill in the art that the amount of drug required for therapeutic effect on administration will, of course, vary with the agent chosen, the nature and severity of the condition and the mammal undergoing treatment, and is ultimately at the discretion of the physician. Furthermore, the optimal quantity and spacing of individual dosages of a drug will be determined by the nature and extent of the therapeutic effects desired, the form, route and site of administration, the particular patient being treated and that such optima can be determined by conventional techniques. It will also be appreciated that the optimal course of treatment, for example, the number of doses given, can be ascertained by those skilled in the art using conventional course of treatment determination tests.

Preferred tablet and capsule formulations in accordance with the invention are set out below in Table 2.

TABLE 2

| Tablet and Capsule Formulations | | |
|---|---|---|
| Material Tablet | Range %/mg by weight of 200 mg tablet | Preferred Range %/mg by weight of 200 mg tablet |
| Dapagliflozin | 0.1 to 70%/0.2 to 140 mg | 1 to 50%/2 to 100 mg |
| Bulking Agent | 2 to 95%/4 to 190 mg | 10 to 85%/20 to 170 mg |
| Lactose | 0 to 95%/0 to 190 mg | 20 to 75%/10 to 100 mg |
| Microcrystalline cellulose | 0 to 95%/0 to 190 mg | 20 to 75%/40 to 150 mg |
| Disintegrant | 0 to 20%/0 to 40 mg | 0.25 to 10%/0.5 to 20 mg |
| Croscarmellose sodium | 0 to 20%/0 to 40 mg | 2 to 10%/4 to 20 mg |
| Crospovidone | 4 to 12%/4 to 20 mg | 6 to 10%/12 to 20 mg |
| Lubricant | 0.1 to 5%/0.2 to 10 mg | 0.2 to 2%/0.4 to 4 mg |
| Magnesium Stearate | 0.1 to 5%/0.2 to 10 mg | 0.2 to 2%/0.4 to 4 mg |
| Anti adherent/glidant Talc, silicon dioxide | 0 to 10%/0 to 20 mg | 1 to 4%/2 to 8 mg |
| Outer Protective Coating Layer | %/mg by weight of 200 mg tablet | %/mg by weight of 200 mg tablet |
| Coating polymer, and optional plasticizer, glidants and color | 0.5 to 50%/1 to 100 mg | 1 to 5%/2 to 10 mg |

Preferred stock granulation formulations (for use in capsules) in accordance with the invention are set out below in Table 3.

TABLE 3

| Material Tablet | Range %/mg by weight of 200 mg tablet | Preferred Range %/mg by weight of 200 mg tablet |
|---|---|---|
| Dapagliflozin | 0.1 to 70%/0.2 to 140 mg | 1 to 50%/2 to 100 mg |
| Bulking Agent/Binder | 2 to 95%/4 to 190 mg | 10 to 85%/20 to 170 mg |
| Microcrystalline cellulose | 1 to 95%/1 to 190 mg | 20 to 75%/10 to 100 mg |
| Pregelatinized starch | 0 to 95%/0 to 190 mg | 20 to 75%/40 to 150 mg |
| Disintegrant | 0 to 20%/0 to 40 mg | 0.25 to 10%/0.5 to 20 mg |
| Sodium Starch glycolate | 0 to 20%/0 to 40 mg | 2 to 10%/4 to 20 mg |
| Lubricant | 0.1 to 5%/0.2 to 10 mg | 0.2 to 2%/0.4 to 4 mg |
| Magnesium Stearate | 0.1 to 5%/0.2 to 10 mg | 0.2 to 2%/0.4 to 4 mg |
| Anti adherent/glidant Talc silicon dioxide | 0 to 10%/0 to 20 mg | 1 to 4%/2 to 8 mg |

Pharmaceutical formulations for use in the methods of the invention in the form of a tablet or capsule can be obtained by a process which includes the steps of:
 a) formulating granules by wet granulation of the SGLT2 inhibitor,
 b) blending the granules with a tabletting aid and diluent,
 c) tabletting the blend thus obtained into tablets, or
 d) loading the granules into capsules.

The mixture used for forming the granules includes a granulating binder. The granulating binder is preferably a polyvinylpyrrolidone such as, for example, a polyvinylpyrrolidone having a molecular weight of 45,000. The polyvinylpyrrolidone can be used in a proportion of 2 to 4% by weight with respect to the final tablet.

After the granulating step, the granules can be sieved and dried.

The granules are then blended with a diluent and tabletting aid. The diluent can be a conventional filler usually used for making tablets, such as microcrystalline cellulose. The tabletting aid can be a conventional material, such as magnesium stearate.

A typical injectable preparation is produced by aseptically placing 50 mg of compounds of structure I into a vial, aseptically freeze-drying and sealing. For use, the contents of the vial are mixed with 2 mL of physiological saline, to produce an injectable preparation.

SGLT2 inhibitor activity of the compounds of the invention can be determined by use of an assay system as set out below.

Assay for SGLT2 Activity

The mRNA sequence for human SGLT2 was cloned by reverse-transcription and amplification from human kidney mRNA, using standard molecular biology techniques. The cDNA sequence was stably transfected into CHO cells, and clones were assayed for SGLT2 activity essentially as described in Ryan et al., 1994, "HK-2: an immortalized proximal tubule epithelial cell line from normal adult human kidney," *Kidney International* 45:48-57. Evaluation of inhibition of SGLT2 activity in a clonally selected cell line was performed essentially as described in Ryan et al., with the following modifications. Cells were grown in 96-well plates for 2-4 days to 75,000 or 30,000 cells per well in F-12 nutrient mixture (Ham's F-12; GIBCO, Long Island, N.Y.), 10% fetal bovine serum, 300 µg/ml Geneticin and penicillin-streptomycin. At confluence, cells were washed twice with 10 mM Hepes/Tris, pH 7.4, 137 mM N-methyl-D-glucamine, 5.4 mM KCl, 2.8 mM $CaCl_2$, 1.2 mM $MgSO_4$. Cells then were incubated with 10 µM [$^{14}$C]AMG and 10 µM inhibitor (final DMSO=0.5%) in 10 mM Hepes/Tris, pH 7.4, 137 mM NaCl, 5.4 mM KCl, 2.8 mM $CaCl_2$, 1.2 mM $MgSO_4$ at 37° C. for 1.5 hr. Uptake assays were quenched with ice cold 1×PBS containing 0.5 mM phlorizin, and cells were then lysed with 0.1% NaOH. After addition of MicroScint scintillation fluid, the cells were allowed to shake for 1 hour, and then [$^{14}$C]AMG was quantified on a TopCount scintillation counter. Controls were performed with and without NaCl. For determination of $EC_{50}$ values, 10 inhibitor concentrations were used over 2 log intervals in the appropriate response range, and triplicate plates were averaged across plates. Ryan et al., Id.

EXAMPLES

The following working Examples are illustrative of the invention. All temperatures are expressed in degrees Centigrade unless otherwise indicated.

Examples 1 to 3

Capsules containing the SGLT2 inhibitor of Formula I (dapagliflozin) were prepared in strengths of 2.5 mg (Example 1), 10 mg (Example 2) and 100 mg (Example 3) (as the non-solvated form) as two-piece, gray opaque size #0 (2.5 mg and 10 mg) and size #00 (for 0 mg) hard gelatin capsules.

Examples 1 and 2

Composition: 25.0 mg of Granulation containing dapagliflozin for Capsules (10.0% w/w as the non-solvated form), filled in Gray, Opaque, Size #0 Capsule Shell.

A. Stock Granulation Composition

| Ingredient | Amount (% w/w) |
| --- | --- |
| Dapagliflozin PGS[1] | 10.0 |
| Pregelatinized Starch, NF | 15.0 |
| Microcrystalline Cellulose, NF[2] | 68.75 |
| Sodium Starch Glycolate, NF | 3.0 |
| Silicon Dioxide, NF | 2.0 |
| Magnesium Stearate, NF[3] | 1.25 |

[1]This amount is expressed in terms of the amount of the dapagliflozin at 100% purity. The exact amount will vary depending on the purity of the dapagliflozin.
[2]The amount of microcrystalline cellulose used will vary depending on the purity of the dapagliflozin.
[3]The preferred amount is 1.25% (w/w). The range is 1.25-1.50% (w/w).

The stock granulation of Part A and the Example 1 and Example 2 capsules were prepared according to the following procedures.

Example 1

B. Example 1 Stock Granulation Procedure

1. Screen dapagliflozin.
2. Screen silicon dioxide.
3. Mix silicon dioxide with dapagliflozin in a suitable blender.
4. Screen pregelatinized starch and microcrystalline cellulose, if necessary.
5. Add ingredients from Step 4 to a suitable blender.
6. Add mixture from Step 3 to the blend from Step 5, and mix.
7. Screen sodium starch glycolate.
8. Add ingredient from Step 7 to the blend from Step 6, and mix.
9. Screen the blend from Step 8, and mix.
10. Screen portion of magnesium stearate.
11. Add ingredient from Step 10 to the blend from Step 9, and mix.
12. Densify the blend from Step 11.
13. Reduce the densified blend Step 12.
14. Screen the remaining portion of magnesium stearate.
15. Add ingredient from Step 14 to the granulation from Step 13, and mix.

C. Example 1 Product: Dapagliflozin Capsule, 2.5 mg (as the Non-Solvated Form)

1. Fill empty capsule shells with sufficient Example 1 Part A stock granulation for capsules (10.0%) w/w (as the non-solvated form), to provide 2.5 mg capsules.
2. De-dust the capsules.

Example 2

Product: Dapagliflozin Capsule, 10 mg (as the Non-Solvated Form)

1. Fill empty capsule shells with Example 1 Part A stock granulation for capsules (10.0% w/w as the non-solvated form), to provide 10 mg capsules.
2. De-dust the capsules.
3. Weight sort the capsules.

The Example 1 (2.5 mg) and Example 2 (10 mg) capsules are used in treating obesity.

Example 3

Dapagliflozin Capsule, 100 mg (as the Non-Solvated Form)

Composition: 438.6 mg of dapagliflozin (Example 3 Part A) Stock Granulation for Capsules (22.8% w/w as the non-solvated form), filled in Gray, Opaque, Size #0 Capsule Shell.

A. Stock Granulation Composition

| Ingredient | Amount (% w/w) |
| --- | --- |
| Dapagliflozin PGS[1] | 22.8 |
| Pregelatinized Starch, NF | 15.0 |
| Microcrystalline Cellulose, NF[2] | 55.95 |
| Sodium Starch Glycolate, NF | 3.0 |
| Silicon Dioxide, NF | 2.0 |
| Magnesium Stearate, NF[3] | 1.25 |

[1]This amount is expressed in terms of the amount of the dapagliflozin at 100% purity. The exact amount will vary depending on the purity of the dapagliflozin.
[2]The amount of microcrystalline cellulose used will vary depending on the purity of the dapagliflozin.
[3]The preferred amount is 1.25% (w/w). The range is 1.25-1.50% (w/w).

The stock granulation of Part A and the Example 3 capsules were prepared according to the following procedures.

B. Stock Granulation Procedure

1. Screen silicon dioxide.
2. Mix silicon dioxide with dapagliflozin in a suitable blender.
3. Screen the blend from Step 2, and mix again.
4. Screen pregelatinized starch and microcrystalline cellulose, if necessary.
5. Add ingredients form Step 4 to the blend from Step 3, and mix.
6. Screen sodium starch glycolate.
7. Add ingredient from Step 6 to the blend from Step 5, and mix.
8. Screen a portion of magnesium stearate.
9. Add ingredient from Step 8 to the blend from Step 7, and mix.
10. Densify the blend from Step 9.
11. Reduce the densified blend from Step 10.
12. Screen the remaining portion of magnesium stearate.
13. Add ingredient from Step 12 to the granulation from Step 11, and mix.

C. Example 3 Product: Dapagliflozin Capsule, 100 mg (as the Non-Solvated Form)

1. Fill empty capsule shells with Example 3 stock granulation for capsules (22.8% w/w as the non-solvated form).
2. De-dust the capsules.
3. Weight sort the capsules.

Examples 4 to 6

Tablets containing the SGLT2 inhibitor of formula Ia (dapagliflozin (S)-propylene glycol solvate (PGS) (or dapagliflozin PGS) were prepared in strengths of 2.5 mg (Example 4), 10 mg (Example 5) and 50 mg (Example 6) as described below.

Example 4

Product: Dapagliflozin PGS Tablet, 2.5 mg

A. Tablet Composition

| Ingredient | Amount |
| --- | --- |
| Dapagliflozin PGS[1] | 3.075 mg |
| Microcrystalline Cellulose, NF[2] | 67.113 mg |
| Lactose Anhydrous, NF | 25.000 mg |
| Crospovidone, NF | 8.750 mg |
| Croscarmellose Sodium, NF | 3.750 mg |
| Talc, USP | 12.500 mg |
| Silicon Dioxide, NF | 2.875 mg |
| Magnesium Stearate, NF[3] | 1.938 mg |

[1]Dapagliflozin PGS is a propylene glycol solvate. The amount of non-solvated dapagliflozin is theoretically equivalent to 81.29% of dapagliflozin PGS. The actual amount of dapagliflozin PGS will depend on the "As Is" purity of the drug.
[2]This is the compensating excipient. The amount used may vary depending on the "As Is" purity of the drug and/or the actual amount of magnesium stearate used.
[3]The target amount is 1.94 mg. Acceptable range is 1.55-2.33 mg.

The stock granulation of Part A and the Example 4 tablets were prepared according to the following procedures.

B. Stock Granulation Procedure

1. Deaggregate dapagliflozin PGS and magnesium stearate separately using a suitable screen.
2. Mix dapagliflozin PGS with a portion of microcrystalline cellulose in a suitable mixer and transfer it into a suitable blender.
3. "Dry Rinse" the mixer used for mixing Step 2 with a portion of microcrystalline cellulose.
4. Add the blend from Step 3 to the blend from Step 2.
5. Mix the mixture from Step 4 with remaining microcrystalline cellulose, portion of crospovidone, portion of croscarmellose sodium, portion of silicon dioxide and lactose anhydrous.
6. Add talc and intragranular magnesium stearate to the mixture from Step 5 and mix.
7. Compact the powder blend from Step 6.
8. Reduce compact from Step 7 to form granules.
9. Mix the granules from Step 8 with remaining amounts of crospovidone, croscarmellose sodium and silicon dioxide.
10. Mix the granules from Step 9 with remaining amount of magnesium stearate.

C. Example 4 Product: Dapagliflozin PGS Tablet, 2.5 mg

1. Setup the tabletting equipment
2. Compress the Example 4 stock granulation into tablets (2.46% w/w), (2.5 mg). .

Example 5

Product: Dapagliflozin PGS Tablet, 10 mg

A. Tablet Composition

| Ingredient | Amount |
| --- | --- |
| Dapagliflozin PGS[1] | 12.300 mg |
| Microcrystalline Cellulose, NF[2] | 57.888 mg |
| Lactose Anhydrous, NF | 25.000 mg |
| Crospovidone, NF | 8.750 mg |
| Croscarmellose Sodium, NF | 3.750 mg |
| Talc, USP | 12.500 mg |
| Silicon Dioxide, NF | 2.875 mg |
| Magnesium Stearate, NF[3] | 1.938 mg |

[1]Dapagliflozin PGS is a propylene glycol solvate. The amount of non-solvated dapagliflozin PGS is theoretically equivalent to 81.29% of dapagliflozin PGS. The actual amount of dapagliflozin PGS will depend on the "As Is" purity of the drug.
[2]This is the compensating excipient. The amount used may vary depending on the "As Is" purity of the drug and/or the actual amount of magnesium stearate used.
[3]The target amount is 1.94 mg. Acceptable range is 1.55-2.33 mg.

The stock granulation of Part A and the Example 5 tablets were prepared according to the following procedures.

B. Stock Granulation Procedure

1. Deaggregate dapagliflozin PGS and magnesium stearate separately using a suitable screen.
2. Mix microcrystalline cellulose, dapagliflozin PGS portion of crospovidone, portion of croscarmellose sodium, portion of silicon dioxide and lactose anhydrous in a suitable blender.
3. Add talc and intragranular magnesium stearate to the mixture from Step 2 and mix in a suitable blender.
4. Compact the powder blend from Step 3.
5. Reduce compact from Step 4 to form granules.
6. Mix the granules from Step 5 with remaining amounts of crospovidone, croscarmellose sodium and silicon dioxide.
7. Mix the granules from Step 6 with remaining amount of magnesium stearate.

C. Example 5 Product: Dapagliflozin Propylene Glycol Solvate (PGS) Tablet, 10 mg 1. Setup the tabletting equipment.
2. Compress the Example 5 stock granulation into tablets (9.84% w/w).

Example 6

Product: Dapagliflozin PGS Tablet, 50 mg

A. Tablet Composition

| Ingredient | Amount |
| --- | --- |
| Dapagliflozin PGS[1] | 61.660 mg |
| Microcrystalline Cellulose, NF[2] | 114.090 mg |
| Lactose Anhydrous, NF | 62.600 mg |
| Crospovidone, NF | 21.910 mg |
| Croscarmellose Sodium, NF | 9.390 mg |
| Talc, USP | 31.300 mg |
| Silicon Dioxide, NF | 7.200 mg |
| Magnesium Stearate, NF[3] | 4.850 mg |

[1]The amount shown is based on the amount of dapagliflozin PGS at 100% purity. The exact amount may vary depending on the "As Is" purity of the dapagliflozin PGS.
[2]This is the compensating excipient. The amount used may vary depending on the "As Is" purity of the drug and/or the actual amount of magnesium stearate used.
[3]The target amount is 4.85 mg. Acceptable range is 3.76-5.95 mg.

The stock granulation of Part A and the Example 6 tablets were prepared according to the following procedures.

B. Stock Granulation Procedure

1. Mix dapagliflozin PGS microcrystalline cellulose, lactose anhydrous, crospovidone, croscarmellose sodium, talc and silicon dioxide in a suitable blender.
2. Pass the mixture from Step 1 through a suitable mill.
3. Determine the yield from Step 1 and calculate the amount of magnesium stearate required.
4. Mix the mixture from Step 2 in a suitable blender.
5. Mix the mixture from Step 4 with magnesium stearate.
6. Dry granulate the powder blend from Step 5.
7. Size the granulation from Step 6.
8. Determine the yield based on Step 7.
9. Mix the granules from Step 8 with remaining amount of crospovidone, croscarmellose sodium and silicon dioxide.
10. Mix the granules from Step 9 with remaining amount of magnesium stearate.

C. Example 6 Product: Dapagliflozin PGS Tablet, 50 mg

1. Setup the tabletting equipment.
2. Compress the Example 6 stock granulation (19.7% w/w), into tablets (50 mg).

Example 7

SGLT2 Inhibitor Dapagliflozin PSG Increases Urinary Excretion of Glucose in Healthy Subjects The glucosuric effects of dapagliflozin PGS results in significant loss of calories in the urine as compared to a known SGLT2 inhibitor (GSK 869,682). As seen in FIG. 1, the results of an indirect comparison of two single ascending dose studies of SGLT2 inhibitors are shown. The panel at the top of FIG. 1 shows the amount of glucose excretion/day within 24 hours in healthy subjects taking 50, 100, 200 or 500 mg of GSK 869,682. The panel at the bottom shows the amount of glucose excretion/day within 24 hours in healthy subjects taking 5, 20, 50 or 100 mg of dapagliflozin PGS.

In a similar experiment, the effects of the C-arylglucoside dapagliflozin PGS and two O-arylglucosides on urine glucose excretion in healthy individuals were compared. The results are shown in Table 4.

TABLE 4

Urinary Glucose Excretion over 24 hr in Healthy Normal Volunteers Following Administration of Selected SGLT2 Inhibitors

| Drug | Dose | Glucose Output over 24 hr |
|---|---|---|
| Sergliflozin-A (O-glucoside)* | 200 mg | 12 g |
|  | 500 mg | 17 g |
| AVE 2268 (O-glucoside) | 1200 mg | 14 g |
|  | 2000 mg | 21 g |
| Dapagliflozin (C-glucoside) | 5 mg | ~32 g |
|  | 20 mg | ~64 g |

*Sergliflozin-A (GSK 869682) has the following structure

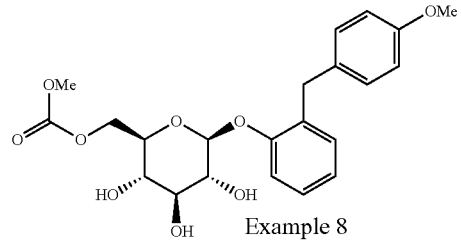

Example 8

Figure 2:
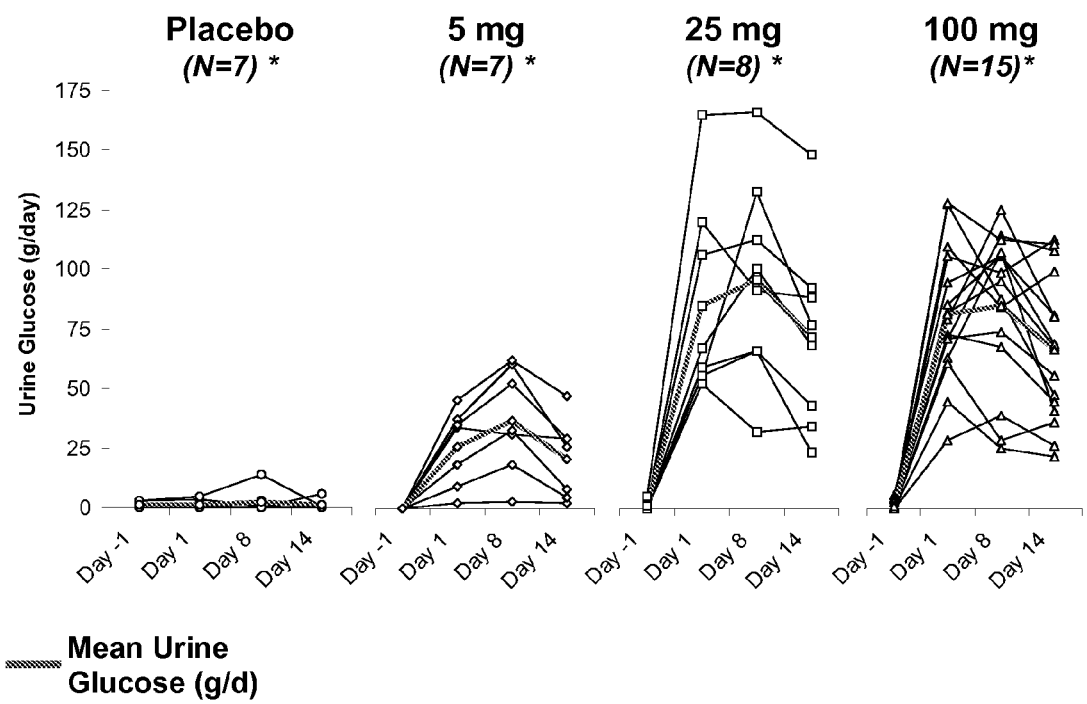
FIG. 2 shows a graph depicting urine glucose excretion in diabetic subjects treated with different doses of dapagliflozin PGS.

SGLT2 Inhibitor Dapagliflozin PGS Increases Urinary Excretion of Glucose Over a 24 Hour Period in Patients with Diabetes In a separate study, patients with diabetes were treated with dapagliflozin PGS at dose of 5, 25, or 100 mg or treated with placebo. The amount of urinary glucose excretion (g/day) was plotted as a function of time and is shown in FIG. 2. The levels of urine glucose of all subjects are shown in the plot and the mean urine glucose is in the darker lines. Compared to subjects treated with placebo, subjects treated with dapagliflozin PGS showed higher levels of urine glucose excretion.

Example 9

Figure 3:
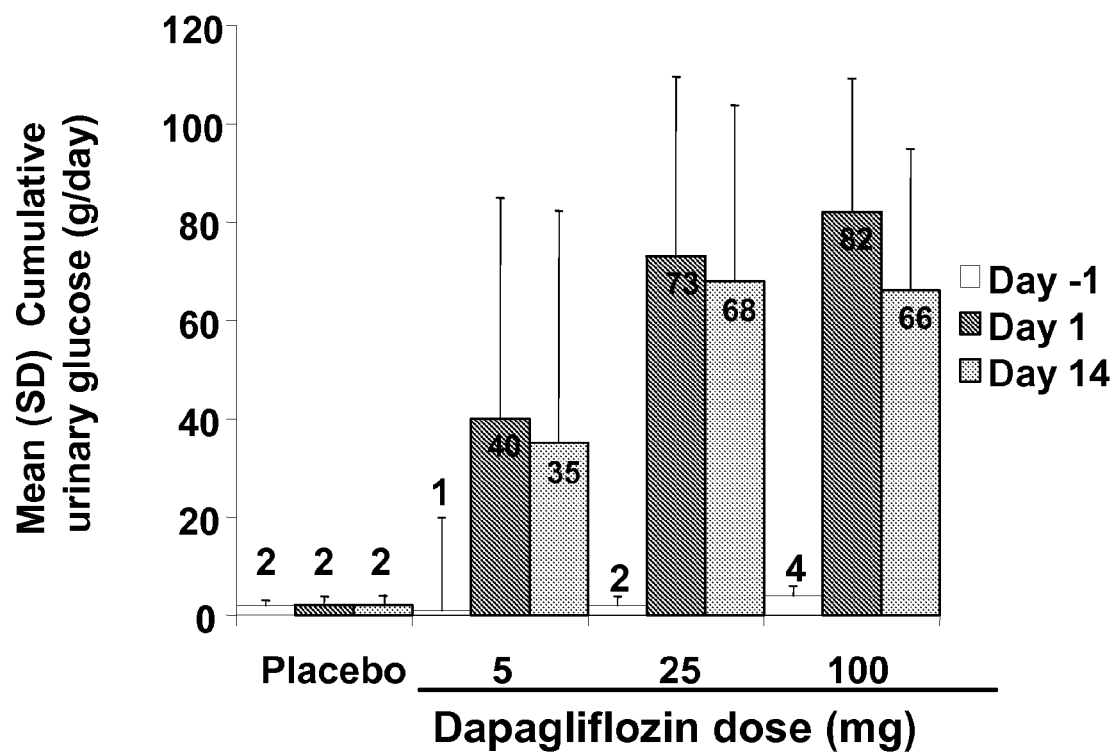
FIG. 3 shows a bar graph depicting urine glucose excretion in diabetic subjects treated with different doses of dapagliflozin PGS.

SGLT2 Inhibitor Dapagliflozin can be Used for Treating Kidney Stones by Increasing Urine Volume Over Time C-aryl glucoside SGLT2 inhibitors are known to reduce blood glucose levels in diabetic patients, see U.S. Pat. No. 6,774,112, which is incorporated herein by reference in its entirety, but not known to increase urine volume. In this experiment, the effects of dapagliflozin PGS on glucosuria and urine volume were examined. 47 drug-naïve or metformin-treated type 2 diabetic patients with fasting serum glucose levels no greater than 240 mg/dL were included in the study. Metformin reduces plasma glucose concentration by non-renal mechanisms and is not known to induce glucosuria. The patients received various amounts of dapagliflozin PGS or placebo on day zero. On day 1 and day 14, the patients were examined for the levels of glucosuria and changes in urine volumes. As shown in FIG. 3, urinary glucose levels increased within a 24-hour time period in dapagliflozin-treated, but not in placebo-treated, subjects. Within the dapagliflozin-treated group, the constant rate of glucosuria over 24 hours was estimated to be about 2 g/hr and 48 g/d (5 mg dapagliflozin PGS) and about 3 g/hr and 72 g/d (25 mg and 100 mg dapagliflozin PGS). Dose-dependent reduction in fasting serum glucose (FSG) levels, and reduced postprandial glucose levels in oral glucose tolerance tests (OGTT) were also observed in dapagliflozin-treated patients. Although both FSG and OGTT responses improved over a two-week period of time, no increase in urine volumes was apparent during the same time period.

Urine volume increases were observed in patients with prolonged treatment of dapagliflozin PGS. In a separate experiment, diabetic patients were treated with 2.5 mg, 5 mg, 10 mg, 20 mg, and 50 mg dapagliflozin PGS for 12 weeks (N=389, body mass index (BMI)>30, with glycosylated hemoglobin HbAlC levels around 7.7-8.0%). After 12 weeks of treatment, the patient excreted 50-60 g glucose in urine every day, and showed improved OGT and reduced HbAlC levels (0.71-0.9%, similar to patients treated with 1500 mg metformin, which showed HbAlC levels at 0.73%).

Significantly, the patients treated with dapagliflozin PGS for 12 weeks showed a 5-20% increase in urine volume. See Table 5. Thus, dapagliflozin increased urine volume over time and can be used as a treatment or prevention for kidney stones.

TABLE 5

Patients received dapagliflozin PGS treatment for 12 weeks exhibited increased urine volume as compared to patients received placebo

|  | dapagliflozin PGS (mg) | | | | | Placebo | Metformin |
|---|---|---|---|---|---|---|---|
|  | 2.5 n = 59 | 5 n = 58 | 10 n = 47 | 20 n = 59 | 50 n = 56 | N = 54 | N = 56 |
| Urine Output (mL), change from baseline at week 12 | 106.62 ± 606.88 | 339.96 ± 551.34 | 374.49 ± 741.62 | 374.91 ± 723.13 | 470.26 ± 797.51 | −111.52 ± 655.40 | −95.84 ± 775.41 |
| P-value vs. placebo | 0.09 | 0.0004 | 0.002 | 0.0009 | 0.0002 |  |  |

Values are means ± standard deviation. The mean daily 24-hour urine volumes at baseline were between 1.9 and 2.2 L per day.

What is claimed is:

1. A method for treating kidney stones in a mammal comprising administering to the mammal in need of such treatment a therapeutically effective amount of a sodium glucose transporter 2 (SGLT2) inhibitor, wherein the SGLT2 inhibitor is

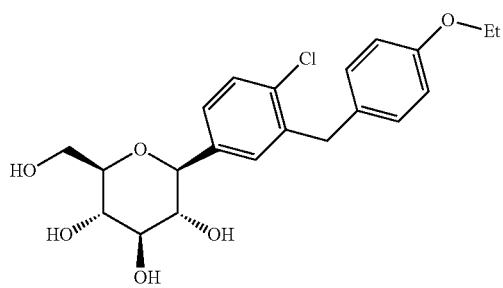 [SMILES: CCOc1ccc(Cc2cc([C@@H]3O[C@H](CO)[C@@H](O)[C@H](O)[C@H]3O)ccc2Cl)cc1]

or a prodrug ester thereof or a propylene glycol solvate thereof, further comprising administering to the mammal an anti-diuresis hormone (ADH) antagonist, wherein the ADH antagonist is administered before, after, or concurrently with the SGLT2 inhibitor.

2. The method according to claim 1, wherein the mammal is a human.

3. The method according to claim 1, said method further comprising administering to the mammal a supply of carbohydrate, wherein the supply of carbohydrate is administered before, after, or concurrently with the SGLT2 inhibitor.

4. The method according to claim 1, further comprising administering to the mammal a supply of carbohydrate, wherein the supply of carbohydrate is administered before, after, or concurrently with the SGLT2 inhibitor.

5. The method according to claim 1, wherein the SGLT2 inhibitor is administered in an amount sufficient to reduce kidney stones without inducing hypoglycemia.

6. The method according to claim 1 wherein the SGLT2 inhibitor is

Compound Ia

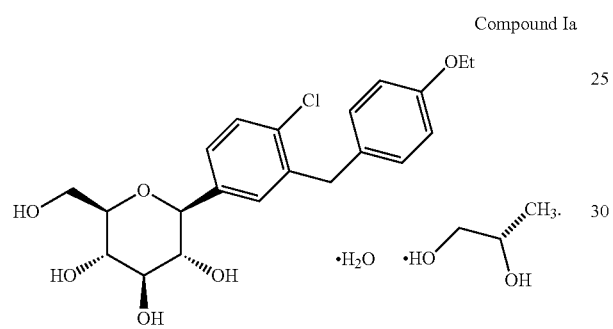

7. A pharmaceutical composition comprising

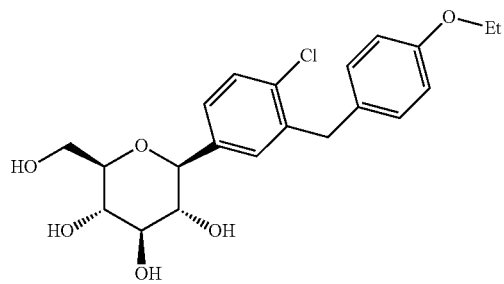 [SMILES: CCOc1ccc(Cc2cc([C@@H]3O[C@H](CO)[C@@H](O)[C@H](O)[C@H]3O)ccc2Cl)cc1]

or a prodrug ester thereof or a propylene glycol solvate thereof and an anti-diuresis hormone (ADH) antagonist.

8. The pharmaceutical composition of claim 7, further comprising a supply of carbohydrate.

9. The method of claim 1 wherein the SGLT2 inhibitor increases urine volume.

10. The method according to claim 1, wherein the mammal does not suffer from hyperglycemia.

11. The method according to claim 3, wherein the supply of carbohydrate is administered concurrently with the SGLT2 inhibitor at a rate in the range of about 30 to about 270 g carbohydrate per day.

\* \* \* \* \*